(12) United States Patent
Attie et al.

(10) Patent No.: US 7,863,301 B2
(45) Date of Patent: Jan. 4, 2011

(54) POTENTIATORS OF INSULIN SECRETION

(75) Inventors: Alan D. Attie, Madison, WI (US); Mary E. Rabaglia, Lodi, WI (US); Ronald T. Raines, Madison, WI (US); Mark Gray-Keller, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 337 days.

(21) Appl. No.: 10/922,442

(22) Filed: Aug. 20, 2004

(65) Prior Publication Data
US 2005/0059711 A1 Mar. 17, 2005

Related U.S. Application Data

(60) Provisional application No. 60/496,802, filed on Aug. 21, 2003.

(51) Int. Cl.
*A61K 31/44* (2006.01)
(52) U.S. Cl. ...................... 514/354; 514/866
(58) Field of Classification Search ................ 514/354, 514/866
See application file for complete search history.

(56) References Cited

U.S. PATENT DOCUMENTS

| 2,980,687 | A |   | 4/1961 | Carmack et al. |
| 4,717,727 | A | * | 1/1988 | Gunzler et al. ............. 514/354 |
| 5,427,940 | A |   | 6/1995 | Newgard |
| 5,801,193 | A | * | 9/1998 | Ojo-Amaize et al. ........ 514/475 |
| 5,914,339 | A |   | 6/1999 | Sum et al. |
| 5,993,799 | A |   | 11/1999 | Newgard |
| 6,020,361 | A |   | 2/2000 | Venkatesan |

FOREIGN PATENT DOCUMENTS

| JP | 61171417 A | 8/1986 |
| JP | 2000/351731 A | 12/2000 |
| WO | WO 99/01432 A | 1/1999 |
| WO | WO 01/23347 A1 | 4/2001 |
| WO | WO 01/92273 A2 | 12/2001 |
| WO | WO 02/39997 A2 | 5/2002 |
| WO | WO 03/053915 A2 | 7/2003 |

OTHER PUBLICATIONS

Blank, B. et al., Mercapto Heterocyclic carboxylic acids, analogues of 3-mercaptopicolinic acid, J Med. Chem. 20(4):572-576 (1977).
Blank, B. et al, Mercaptopyridinecarboxylic acids, synthesis and hypoglycemic activity, J. Med. Chem. 17(10):1065-1071 (1974).
Schneid, C., In vivo induction of insulin secretion by ornithine a-ketoglutarate: Involvement of nitric oxide and glutamine, Metabolism 52(3):344-350 (2002).
Kikuchi, A. et al., Stimulatory effect of a sulfonylurea analogue and its polymer conjugate on insulin secretion from rat islets, Biotechnol. Prog. 10:630-635 (1994).
Asfari, M., et al., 1992"Establishment of 2-Mercaptoethanol-Dependent Differentiated Insulin-Secreting Cell Lines," Endocrinology 130:167-178.
Best, L. (1997) "Glucose and alpha-ketoisocaproate induce transient inward currents in rat pancreatic beta cells," Diabetologia 40:1-6.
Branstrom, R., et al., (1998) "Direct Inhibition of the Pancreatic Beta-Cell ATP-Regulated Potassium Channel by Alpha-Ketoisocaproate," J. Biol. Chem. 273:14113-14118.
Bryan, J., et al., (1999) "Sulfonylurea receptors: ABC transporters that regulate ATP-sensitive K+ channels," Biochim. Biophys. Acta 1461:285-303.
Gao, Z., et al., (2003) "Distinguishing Features of Leucine and Alpha-Ketoisocaproate Sensing in Pancreatic Beta-Cells," Endocrinology 144:1949-1957.
Gembal, M., et al., (1992) "Evidence that glucose can control insulin release independently from its action on ATP-sensitive K+ channels in mouse B cells," J. Clin. Invest. 89:1288-1295.
Hanson, R.L., et al. (1998) "An Autosomal Genomic Scan for Loci Linked to Type II Diabetes Mellitus and Body-Mass Index in Pima Indians," Am. J. Hum. Genet. 63:1130-1138.
Hohmeier, H.E., et al., (2000) "Isolation of INS-1-Derived Cell Lines With Robust ATP-Sensitive K+ Channel-Dependent and -Independent Glucose-Stimulated Insulin Secretion" Diabetes 49:424-430.
Malaisse, W.J., et al., (1981) "The stimulus-secretion coupling of amino acid-induced insulin release. Metabolic interaction of L-glutamine and 2-ketoisocaproate in pancreatic islets." Biochim. Biophys Acta 677:39-49.
Obici, S., et al., (2001) "Central Administration of Oleic Acid Inhibits Glucose Production and Food Intake," Rapid Publication.
Obici, S., et al., (2002) "Hypothalamic insulin signaling is required for inhibition of glucose production," Nature Medicine 8:1376-1382.
Obici, S., et al., (2003) "Inhibition of hypothalamic camitine palmitoyltransferase-1 decreases food intake and glucose production," Nature Medicine 9:756-761.
Persuad, S.J., et al, (1999) "Tyrosine kinases play a permissive role in glucose-induced insulin secretion from adult rat islets," Journal of Molecular Endocrinology 22:19-28.
Stanley, C.A., et al., (1998) "Hyperinsulinism and hyperammonemia in infants with regulatory mutations of the glutamate dehydrogenase gene," N. Engl. J. Med. 338:1352-1357.
Straub, S.G., et al., (2002) "Glucose-stimulated signaling pathways in biphasic insulin secretion," Diabetes Metab. Res. Rev. 18:451-463.
Straub, S.G., et al., (2003) "Stimulation of insulin secretion by denatonium, one of the most bitter-tasting substances known," Diabetes 52:356-364.

* cited by examiner

*Primary Examiner*—Kevin Weddington
(74) *Attorney, Agent, or Firm*—Quarles & Brady LLP

(57) ABSTRACT

The present invention relates to a recognition that an analog of αKG can increase glucose-induced insulin secretion in vitro and in vivo in animals, particularly in mammals, and more particularly in humans and in rodents. By employing the methods of the invention, insulin secretion can be increased.

1 Claim, 4 Drawing Sheets

POTENTIATORS OF INSULIN SECRETION

CROSS-REFERENCE TO RELATED APPLICATION

This application claims the benefit of U.S. Provisional Application No. 60/496,802 filed Aug. 21, 2003.

STATEMENT REGARDING FEDERALLY SPONSORED RESEARCH OR DEVELOPMENT

This invention was made with U.S. government support awarded by the following agency: NIH DK58037. The United States has certain rights in this invention.

BACKGROUND OF THE INVENTION

Pancreatic β cells secrete insulin in response to elevated amounts of blood glucose and other blood borne metabolites termed "secretagogues." Glucose is delivered to body tissues in part via transporters that respond to insulin. Insulin reduces blood glucose by stimulating its removal from the bloodstream and by inhibiting glucose production by the liver. In addition to glucose, other molecules stimulate β-cells to secrete insulin. These include amino acids, α-ketoacids and mitochondrial metabolites. Collectively, these secondary secretagogues can account for as much as 50% of all insulin secreted.

The control of blood glucose is initiated by Glut2-dependent glucose uptake by pancreatic β-cells. Inside the cell, glucose is metabolized to yield ATP, which causes ATP-sensitive $K^+$ ion channels ($K_{ATP}$) to close, blocking the efflux of $K^+$ ions and depolarizing the membrane potential. This depolarization opens voltage-gated $Ca^{2+}$ ion channels ($V_{Ca}$), leading to a rise in intracellular $Ca^{2+}$, which triggers vesicle mobilization and insulin secretion.

A genetically inherited condition characterized by higher than normal glutamate dehydrogenase enzyme activity arises from any of several mutations at the site of GTP-mediated suppression of the enzyme. The enzyme catalyzes oxidative glutamate deamination and produces ammonia, α-ketoglutarate (αKG), and reducing equivalents. Humans having the condition exhibit hyperammonemia, hyperinsulinemia, and hypoglycemia. The mechanism by which excessive glutamate dehydrogenase activity increases insulin secretion is not known. The conventional wisdom is that stimulation of insulin release requires metabolism of αKG.

αKG is a Krebs cycle intermediate that can be oxidatively decarboxylated to form succinate, an insulin secretagogue. αKG is also a stoichiometric cofactor of various αKG-dependent hydroxylase enzymes, including prolyl-4-hydroxylases which have a variety of substrates, the best studied being collagen. Prolyl-4-hydroxylases also regulate hydroxylation at a single proline residue on Hypoxia Inducible Factor-1α (HIF-1α), a transcription factor that regulates a potassium ATP ($K_{ATP}$) channel involved in insulin secretion from β cells.

Cellular αKG is formed by glutamate dehydrogenase (GDH) and in the citric acid cycle via isocitrate dehydrogenase as well as by the branched chain aminotransferase (BCAT) reaction wherein no reducing equivalents are produced. In this reaction, an α-ketoacid and an α-amino acid are interconverted into their corresponding amino- and α-ketoacids. α-ketoisocaproic acid (KIC) is transaminated using an amine group from glutamate to form leucine. In the process, glutamate loses an amine group and forms αKG. KIC-induced hypersecretion of insulin is prevented by blocking the transamination of KIC (using, e.g., BCAT inhibitor methyl-leucine) to leucine and the attendant formation of αKG. αKG formation may be part of a signaling cascade that leads to chronic insulin hypersecretion. When applied to isolated pancreatic β-cells, KIC is known to cause depolarization of the cell membrane voltage, leading to generation of action potentials, increase in cytosolic $Ca^{2+}$ ion concentration and increased insulin secretion. KIC-dependent depolarization is known to be due to a direct inhibition of $K_{ATP}$. In intact β-cells the flow of $K^+$ ions through $K_{ATP}$ is likely the current that dominates the resting membrane potential. Accordingly, agents that modulate $K_{ATP}$ channel activity will necessarily alter membrane potential.

Persaud, S. J. et al., *J. Molec. Endocrin.* 22:19-28 (1999) discloses that protein tyrosine kinase inhibitors genistein and tyrphostin A47 inhibited KIC-stimulated insulin release without affecting glucose metabolism. Persaud et al. suggested that the protein tyrosine kinase inhibitors exert their inhibitory effects distal to closure of ATP-sensitive $K^+$ channels, but proximal to $Ca^{2+}$ entry into β cells, and that the inhibitors act at the site of the voltage-dependent $Ca^{2+}$ channel that regulates $Ca^{2+}$ influx into β cells following depolarization.

A recently discovered heritable genetic disorder attributable to mutations in the GDH enzyme highlights the physiological importance of αKG-dependent insulin segretagogue activity. The enzyme catalyzes conversion of glutamate to αKG and ammonia. In mutated form, the enzyme causes chronic hyper-insulinemia resulting in severe hypoglycemia. Interestingly, the mutations led to an increase in enzyme activity and over-production of αKG.

It would be advantageous to identify compounds that augment the amount of insulin secretion evoked by glucose and other secretagogues. Such compounds would have therapeutic utility in treating those forms of diabetes caused by insufficient β cell responsiveness to insulin secretagogues.

BRIEF SUMMARY OF THE INVENTION

It is herein proposed for the first time that analogs of αKG can potentiate insulin secretion in animals, particularly in mammals, and more particularly in humans and in rodents. Rodents, particularly mice, provide a standard, art-accepted model system for studying onset and progression of Type II diabetes, such as also occurs in humans. It is herein proposed and demonstrated that αKG and structural analogs thereof directly regulate the activity of $K_{ATP}$ ion channels and thereby provide additional regulation of insulin secretion by enhancing the glucose-dependent regulation of $K_{ATP}$. In a related aspect, therefore, the invention finds particular applicability to treatment of hyperglycemia in individuals having Type II diabetes in a method that comprises the steps of administering to such an individual an effective amount of a suitable structural analog of αKG as described herein and observing an increase in insulin secretion from pancreatic β cells.

The invention is further summarized in that a preferred αKG analog for use in the methods of the invention is 2,4-diethyl pyridine dicarboxylate (DPD), also known as diethyl-2-4-pyridine dicarboxylate, a known and commercially available inhibitor of prolyl-4-hydroxylase activity.

A skilled artisan can arrive at still further solutions for achieving the goals of the methods by selecting and testing putative agents for effectiveness in the methods. It will also be understood that the compound can be administered in a preparation that comprises a plurality of agents, where at least one agent contributes to the overall insulin-controlling effect.

It is an object of the present invention to increase insulin secretion in individuals having hyperglycemia.

It is an advantage of the present invention that the $K_{ATP}$ channel is an accessible and safe target for drug development in this disease area, insofar as the SUR1 regulatory subunit is a known target for sulfonylurea drugs for treating hyperglycemia.

It is another advantage of the present invention that the natural activity of αKG can be effectively mimicked by compounds having suitable structures described herein. The compounds are not subject to the same metabolic processes in vivo as αKG and are therefore not cleared from the system in the same manner or at as rapid a rate.

It is yet another advantage of the present invention that the αKG analogs enhance, or strengthen, glucose-dependent regulation of $K_{ATP}$, stimulating greater insulin secretion at high rather than low glucose concentrations, and thereby reducing the risk of inducing hypoglycemia, a critical liability associated with the sulfonylurea drugs.

It is yet another advantage of the present invention to provide methods for improving insulin secretion in response to glucose and other secretagogues in individuals having inadequate response to these agents.

Other objects, advantages, and features of the invention will become apparent upon consideration of the following detailed description taken in conjunction with the accompanying drawings.

DETAILED DESCRIPTION OF THE INVENTION

Figure 1:
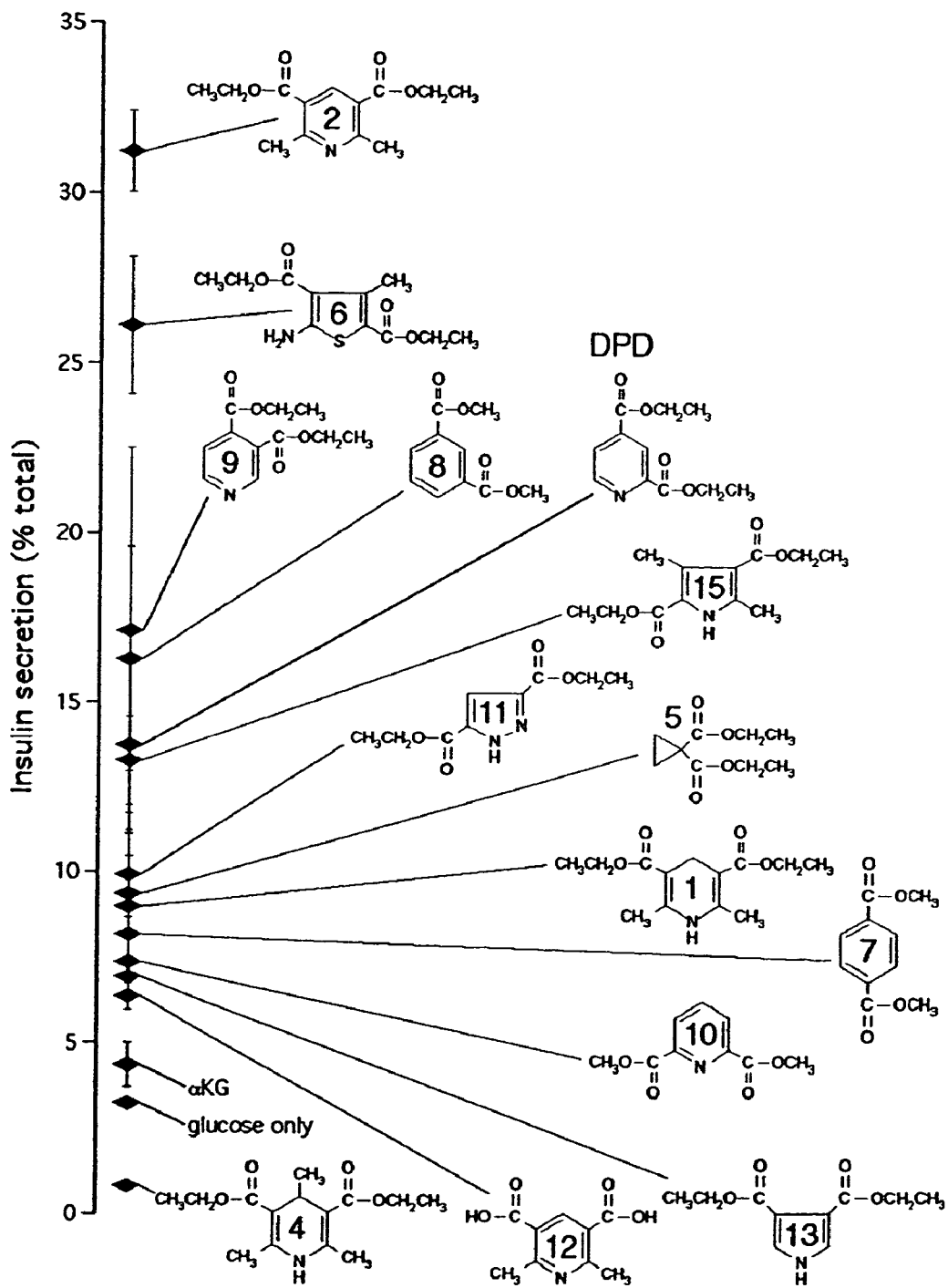
FIG. 1 depicts the ability of various analogs of DPD to increase insulin secretion from pancreatic β cells.

The physiological relevance of insulin secretion from pancreatic β cells elicited by αKG was evaluated. Insulin secretion caused by αKG and DPD, a non-metabolizable analog of αKG, was blocked when the influx of $Ca^{2+}$ ions was suppressed by either bathing cells in $Ca^{2+}$-free medium or by using an L-type $Ca^{2+}$ channel antagonist, nitrendipine. Further, application of $\alpha_2$-adrenergic agonists epinephrine or clonidine greatly suppressed insulin secretion caused by glucose, KIC, αKG or DPD. Taken together, these observations suggest that αKG promotes insulin release utilizing the normal physiological mechanisms of triggered insulin secretion.

Possible targets for the segretagogue action of αKG were examined by reevaluating targets implicated for KIC-dependent increases in insulin secretion, since the effects of KIC are likely exerted through transamination that yields αKG. The inventors hypothesized that αKG, DPD and its analogs stimulate increased insulin release by modulating $K_{ATP}$ directly, since it is believed that the KIC-dependent effect on insulin secretion requires transamination of KIC to yield αKG. To biochemically test this hypothesis the inventors used known drugs to modulate $K_{ATP}$ and then determined whether αKG and DPD could still affect insulin secretion. Diazoxide, a $K_{ATP}$ agonist, completely suppresses the ability of αKG, DPD and KIC to promote insulin release. However, glyburide, a $K_{ATP}$ antagonist, elicits an insulin secretion that is augmented by αKG, DPD or KIC. These results suggest that αKG and DPD inhibit the flow of $K^+$ ions through $K_{ATP}$, leading to membrane depolarization, entry of $Ca^{2+}$ ions and insulin release. In addition, αKG and DPD appear to target a $K_{ATP}$-independent process similar to that shown for glucose.

DPD and structurally related compounds (as disclosed below) that yield more insulin secretion from cells than are preferred agents for use in the methods of the invention. DPD is extremely potent relative to αKG and greatly amplifies the stimulatory effect of glucose on insulin secretion. DPD and structurally related compounds can be used to treat diabetes, particularly when used at a concentration at which the compound does not elicit significant insulin release in the absence of an elevated blood glucose concentration, thereby reducing the risk of hypoglycemia, a problem encountered with the current sulfonylurea medications. In the methods, the agent is formulated with a pharmaceutically acceptable carrier for bioavailability to pancreatic β cells and is administered in an amount sufficient to inhibit KIC-induced insulin secretion in an animal. The compound can be administered by various administration routes including, but not limited to, oral, intravenous, subcutaneous and intraperitoneal routes. The compound should be administered in an amount sufficient to give rise to a concentration of the compound in plasma of between about 0.1 to 1.0 mM.

The method of the invention is considered effective if, after the agent is administered, an increase in insulin comparable to the increases observed using available glyburide compounds (e.g., 47% for repaglinide, 54% for glipizide and 61% for glybenclamide, as reported in Diabetes Care 25:1271 (2002), incorporated herein by reference as if set forth in its entirety). Accordingly an increase of at least about 1.25 fold to less than 3 fold is preferably observed relative to the pretreatment plasma insulin level. Alternatively, and especially in non-human model animals, the effectiveness of the treatment can be tested by comparing freshly explanted pancreatic islet cells that were treated in vivo with like cells explanted from an untreated control to determine whether insulin secretion is increased. Methods for culturing pancreatic islet cells are known in the art.

The ability of various structurally-related compounds to alter insulin secretion in the presence of high glucose was tested in a preliminary structure-activity relationship (SAR) study to elucidate the molecular structures relevant to the insulin segretagogue potential of DPD and other αKG analogs. The compounds tested, shown in FIG. 1, are presented in order of decreasing ability to secrete insulin in an Ins-1 cell assay of the type described below in the Working Example. Each tested compound is commercially available and all were purchased from Sigma-Aldrich. Each compound contained two carboxylate groups. Variables evaluated in this study included the relative position of the carboxylate groups to one another, as well as the presence or absence of a nitrogen or sulfur group, additional R-groups, and esterified carboxy groups.

The preliminary study revealed that:

1. Compounds 2 and 6 were more potent than DPD, eliciting ~31% and 25% secretion respectively, while DPD caused ~14% secretion. This demonstrates that analog compounds having at least twice the potency of DPD can be employed in the methods of the invention.

2. a suitable αKG analog does not require an aromatic nitrogen, as Compound 8 and DPD were equipotent.

3. a suitable αKG analog preferably has a generally planar geometry imposed by an aromatic ring structure, as Compounds 1, 2 and 4 share very similar structures, but the hydrogen group attached to the aromatic nitrogen of inactive Compound 4 destabilizes the planar geometry. This suggests a preferred positioning of the carboxylate groups in a shared plane.

4. in a suitable αKG analog, the carboxylate groups are preferably separated by 3 carbon atoms, as the highest insulin secretion activity is observed using compounds having 3 carbons between the carboxylate groups. Two-carbon separation, as in the case of active Compound 9, or four-carbon separation, as in the case of pyridine-2,5-dicarboxylate can also be acceptable.

5. in a suitable αKG analog, the carboxylate groups are protected by ester groups (or alternatively and less preferably by thioesters or amides). This observation derives from comparing the potency of the most potent Compound 2, which has an ethyl ester group protecting each carboxylate group, and one of the least potent compounds (Compound 12), which differs from Compound 2 only in that it lacks the ethyl ester groups. Because the negative charge associated with un-protected carboxylate groups would prevent Compound 12 from crossing the cellular membrane, this result, in combination with the above-noted observation that diazoxide suppresses insulin secretion by αKG and DPD, suggests that Compound 12 cannot reach a target on the cell interior and that the suitable analogs bind on the inner surface of the cell membrane, particularly to surface-bound $K_{ATP}$.

6. a suitable αKG analog can, but need not comprise an exocyclic amine group, although such a group can be preferred in that it offers a conjugation "handle" for amine-reactive probes such as, but not limited to, a fluorescent or photo-labile group of the sort commonly used to probe binding interactions between a small molecule and its target. For example, Compound 6 is very active and contains an exocyclic amine group.

Structurally, an αKG analog that can function as an insulin segretagogue has a ring core, two carboxyl groups or ester derivatives thereof attached to one or preferably two separate ring atoms, and optionally other side groups. The ring core is preferably a 3- to 6-membered ring and more preferably a 5- or 6-membered aromatic ring. The ring can contain heteroatoms (i.e., non-carbon atoms) such as nitrogen, sulfur, and oxygen atoms. Nitrogen is the preferred heteroatom. The two carboxyl groups or ester derivatives thereof attached to the ring are preferably separated by at least three ring atoms including the two to which they are attached.

Figure 2:
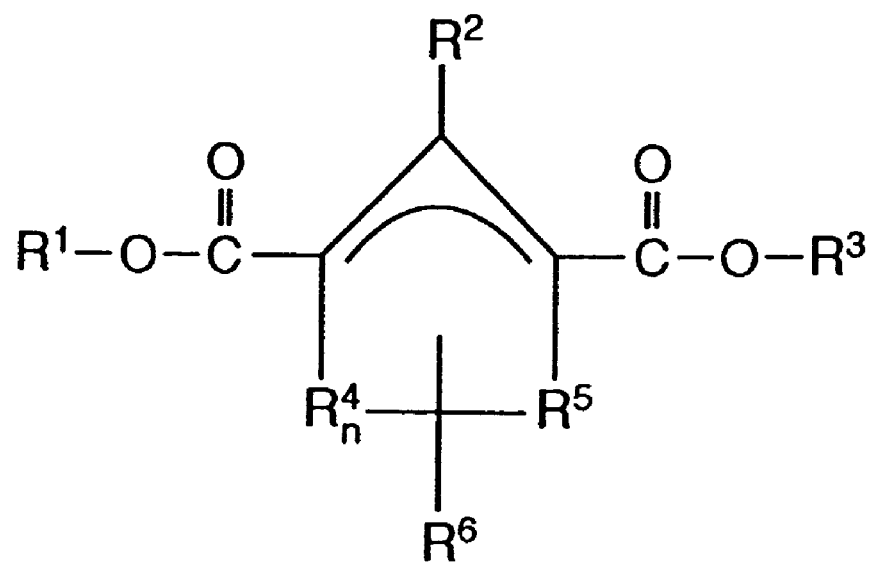
FIG. 2 illustrates an active pharmacophore for an αKG analog that functions as an insulin segretagogue.

Incorporating these observations into a structural model, FIG. 2 illustrates an active pharmacophore for an αKG analog that functions as an insulin segretagogue. The skilled artisan will appreciate the range of compounds having this structure. A systematic process of evaluating the activity of compounds having this active pharmacophore may lead to a more refined pharmacophore. Small groups (e.g., H or $CH_3$) are preferred at R2. In the structural ring that includes R4, R5 and R6, an aromatic five- or six-membered ring is preferred, although larger rings can be employed (n at R4 can be greater than greater than or equal to 1). A six-membered ring can contain 3 double bonds; a five-membered ring can contain a heteroatom (N, O or S) and two double bonds. The heteroatom can be at R4 or at R5 if R6 does not exist. R1 and R3 are also preferably small groups on the order of 1-4 carbons. It will also be appreciated that if a thioester or amide protecting group is employed, the oxygens bound to R1 and R3 would be replaced with sulfur or nitrogen, respectively.

Among the αKG analogs evaluated, DPD is considered a preferred analog because it mimics the stimulation of insulin secretion observed with αKG but is not metabolized like αKG in vivo. Other compounds, especially compounds that cannot be similarly metabolized, having still higher activity can be considered to be still more preferable. Further, if αKG and DPD are applied together at subsaturation levels, the resulting insulin secretion is less than the sum of either compound added alone, suggesting that αKG and DPD impact the same target to promote insulin release. Metabolism of αKG is not required for insulin secretion, although αKG production appears to be required for insulin segretagogue activity under the tested conditions.

The present invention will be more fully understood upon consideration of the following non-limiting examples, performed in vitro in glucose cultures of freshly explanted pancreatic islets cultured with KIC in the presence or absence of the exemplified analog and in cultured cells.

WORKING EXAMPLE

Mouse islets from diabetes-resistant (C57BL/6) or diabetes-susceptible (BTBR) mice were isolated by collagenase digestion, 0.45 mg/ml collagenase (Sigma, Type XI collagenase) in Hanks Balanced Salt Solution (HBSS) containing 0.02% BSA, 0.35 g/L NaHCO3. After two washes in HBSS without collagenase, islets were separated from digested acinar tissue by centrifugation on Ficoll gradients. Islets were then further purified by picking under a dissection microscope.

Insulin released from freshly isolated islets was measured in a static incubation system. Briefly, islets were hand picked with great care to obtain five similar size islets per batch. Minimum of three batches of five islets were used for each incubation condition. Islets were picked and aliquoted at room temperature into batches of five islets in Krebs-Ringer bicarbonate buffer (KRB; 16.7 mM glucose, 5 mM HEPES, 0.2% RIA grade BSA). Islets were picked directly into 12×75 mm glass tubes with the bottom of tube replaced with 62 micron polyester mesh. These "mesh baskets" allow for easy transfer of islets from preincubation media to incubation media with very little disturbance of the islets.

After the islets were aliquoted into the mesh baskets, they were placed in 1 ml preincubation media, KRB containing 1.7 mM glucose, 0.5% BSA, at 37 degrees for 45 minutes. Each tube was gassed with 95% oxygen/5% carbon dioxide, and then capped to maintain pH at 7.4. At the end of the 45 minute preincubation islets in mesh baskets were gently transferred to the incubation media, 1 ml KRB containing 0.5% BSA and the appropriate test agents (glucose concentration was determined by test agents used, but the minimal glucose concentration was 1.7 mM). Incubation period was for 45 minutes at 37 degrees; again each tube was gassed and capped for the duration of the incubation period. This culture is referred to herein as a "glucose culture."

At the end of the incubation period, the mesh basket was removed. The incubation media was frozen at −20 and assayed for insulin using the Linco RIA kit. Islets in the mesh basket were placed into 1 ml acid ethanol for the extraction of islet insulin content. Extracted insulin was diluted with RIA buffer and also assayed for insulin using the Linco RIA kit.

Figure 3:
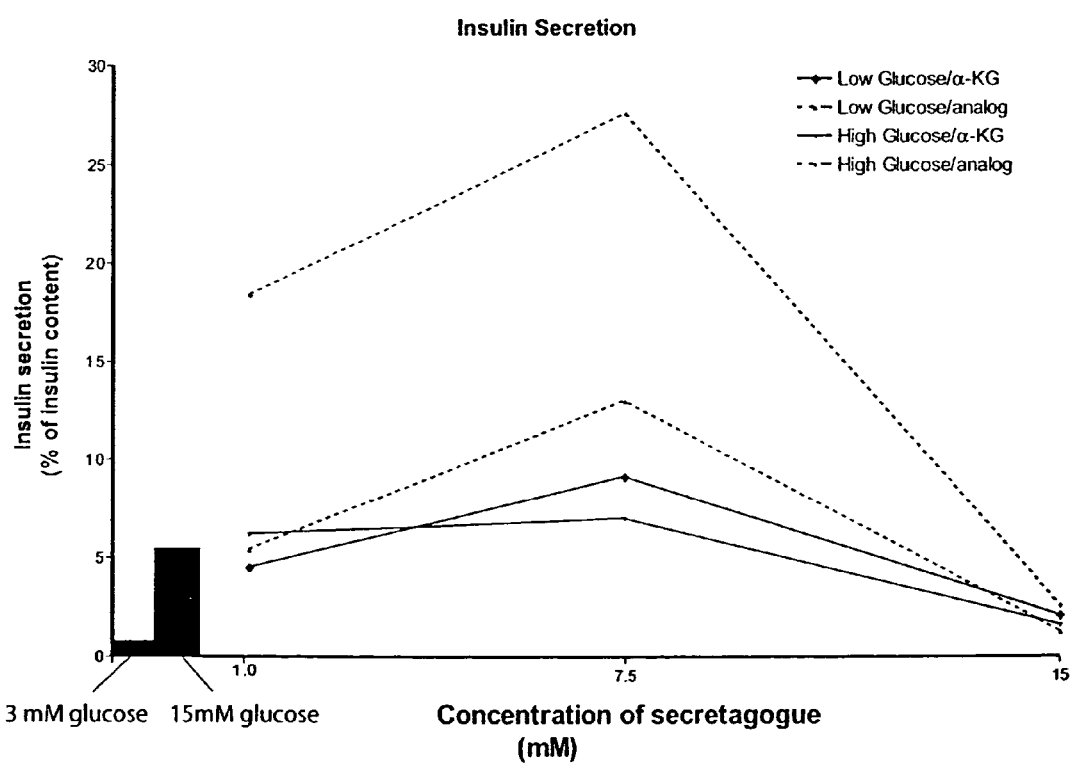
FIG. 3 compares potentiation by αKG and DPD of insulin release from hyperexcitable Newgard Ins-1 cells under low or high glucose conditions.

FIG. 3 depicts fractional insulin release from (a) a cultured Ins-1 insulinoma cell line selected for high insulin secretion response in the presence of glucose (see Hohmeier et al., Diabetes, 49:424 (2000)). FIG. 3 demonstrates in a cell in which the effect of glucose is amplified, that DPD at the indicated concentrations can have a marked positive effect upon insulin secretion in the presence of low (3 mM) or high (15 mM) glucose. The cells were incubated at 3 mM glucose with the indicated concentrations of either αKG or the DPD analog for 2 hours. Then, the cells were incubated for an additional 2 hours in either 3 or 15 mM glucose.

Figure 4:
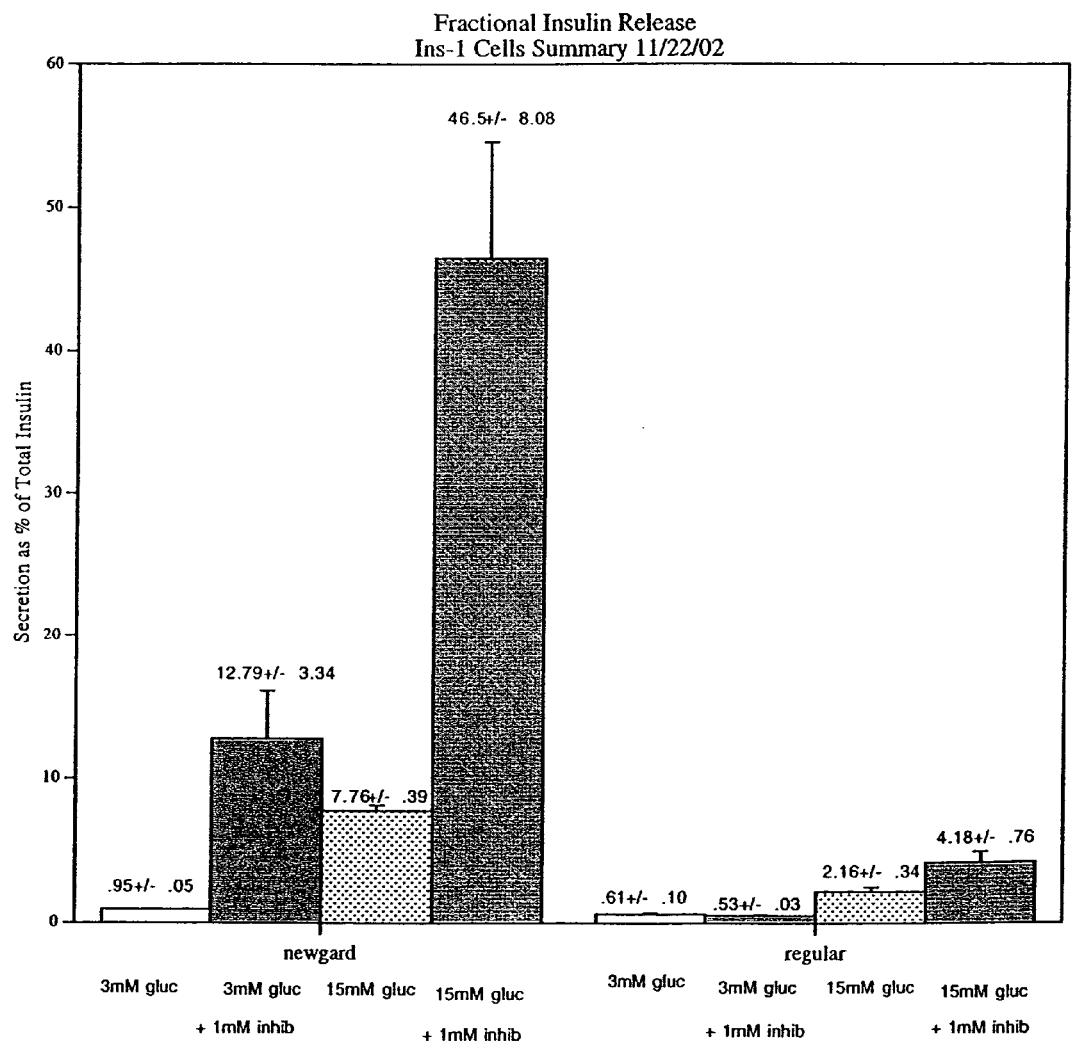
FIG. 4 compares insulin release from two different β cell lines, namely hyperexcitable Newgard Ins-1 cells and standard Ins-1 cells.

In a similar trial, FIG. 4 depicts fractional insulin release from the cells used in FIG. 3 as well as from a commonly used rat Ins-1 beta cell line (see Asfari et al., Endocrinology 130: 167 (1992)). For comparison, while the data from rat Ins-1 cells, shown at the right side of FIG. 4, also evidence an increase in insulin secretion in the presence of DPD, the effect is not as dramatic, thereby demonstrating the desirability of employing a responsive cell line when analyzing the effects αKG and its analogs on insulin secretion.

PROPHETIC EXAMPLE

Intact pancreatic β cells are treated with compounds that promote insulin secretion by suppressing efflux of potassium ions through $K_{ATP}$. Depolarization of the resting membrane potential is observed using micro-electrodes to monitor whole cell voltage, causing voltage-gated calcium ion channels to open, leading to an influx of calcium ions and triggering insulin secretion.

Intact pancreatic β cells are treated with compounds that promote insulin secretion by suppressing efflux of potassium ions through $K_{ATP}$ and with a modulator of $K_{ATP}$ such as diazoxide and glyburide. In the presence of the modulators, insulin secretion is reduced or prevented relative to the secretion from cells not treated with the modulator.

The present invention is not limited to the preceding examples and disclosure, but rather embraces all such modifications and variations as come within the scope of the appended claims.

We claim:

1. A method for treating Type II diabetes in a human or non-human animal caused by insufficient insulin secretion from pancreatic beta cells, the method comprising the steps of:

administering a compound according to the formula

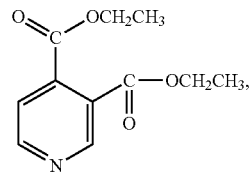

in an amount sufficient to increase glucose-induced insulin secretion; and observing an increase in insulin secretion by pancreatic β cells, whereby the increase is characteristic of increased sensitivity to glucose-induced insulin secretion.

* * * * *